United States Patent [19]

Kushwaha et al.

[11] Patent Number: 5,512,548

[45] Date of Patent: Apr. 30, 1996

[54] CETP INHIBITOR POLYPEPTIDE, ANTIBODIES AGAINST THE SYNTHETIC POLYPEPTIDE AND PROPHYLACTIC AND THERAPEUTIC ANTI-ATHEROSCLEROSIS TREATMENTS

[75] Inventors: Rampratap Kushwaha; Kathleen Born; Henry C. McGill, Jr.; Patrick Kanda; Raymond G. Dunham, all of San Antonio, Tex.

[73] Assignee: Southwest Foundation for Biomedical Research, San Antonio, Tex.

[21] Appl. No.: 193,515

[22] Filed: Feb. 8, 1994

Related U.S. Application Data

[63] Continuation of Ser. No. 811,049, Dec. 19, 1991, abandoned.

[51] Int. Cl.$^6$ .............................. A61K 35/14; C07K 1/00
[52] U.S. Cl. ............................................ 514/12; 530/387.1
[58] Field of Search ............................ 530/387.1; 514/12

[56] References Cited

PUBLICATIONS

Dolphin et al. Lipoprotein . . . programmers, Can. J. Cell Biol. 63:850–869, 1985.
Nishide et al., Inhibition . . . protein, J. Lipid Res, 30:149–158, 1989.
Keul et al., Expression . . . lipoprotein, 28:818–827, 1987.
Merrifield et al., The peptides, Analysis . . . Biology, vol. 2 Academic Press, 1980 pp. 1–284.
Lauer et al. Two . . . Gene, J. Biol. Chem., 263:7277–7286, 1988.
Harlow et al., Antibodies . . . Manual, p. 287, 1988.
Lerner et al., Antibodies . . . Medicine, Adv. Immunol. 36:1–44, 1984.
Koizumi et al., "Atherosclerosis", 58:175–186 (1985).
Yokoyama et al., "Artery" 14(1):43–51 (1986).
Kushwaha et al., "J. of Lipid Research", 31:965–973 (1990).
Son et al., "Biochhimica et Biophysica Acta", 795:473–480 (1984).
Kurasawa et al., "J. Biochem." 98:1499–1508 (1985).
Albers et al., "Lipids", 9:15–26 (1974).
Kohler et al., "Nature", 256:495–497 (1975).
Williams et al., "J. of Chromatography", 308:101–109 (1984).
Kushwaha et al., "J. of Lipid Research", 27:497–507 (1986).
McGill et al., "Arteriosclerosis", 6:651–663 (1986).
Redgrave et al., "Analytical Biochem.", 65:42–49 (1975).
Allain et al., "Clin. Chem.", 20:407–475 (1974).
Laemmli "Nature", 227:680–684 (1970).
Floren et al., "Metabolism", 30:367–375 (1981).
McKinney et al., "J. of Immunological Methods", 96:271–278 (1987).
Cheung et al., "J. of Lipid Research", 23:748–753 (1982).
Barany et al., "The Peptides", 2:1–284 (1980).
Duncan, D. B., "Biometrics", pp. 1–42 (1955).
Pearson et al., "Proc. Natl. Acad. Sci." 85:2444–2448 (1988).

*Primary Examiner*—Jill Warden
*Assistant Examiner*—Benet Prickril
*Attorney, Agent, or Firm*—Cox & Smith Incorporated

[57] ABSTRACT

A polypeptide and analogues thereof inhibit cholesteryl ester transfer protein (CETP). An anti-atherosclerosis composition comprises an anti-atherosclerosis effective amount of the polypeptide and a pharmaceutically-acceptable carrier. An anti-atherosclerosis kit comprises in separate sterile containers at least one unit of the composition containing the polypeptide, one syringe and one needle. An antibody has specificity for the polypeptide of the invention, the baboon CETP 4kD polypeptide inhibitor, the 1–36 amino acid N-terminal fragment of apo C-I, modified apo A-I (MW:31kD) or modified apo E (MW:41kD). A method of preventing atherosclerosis in a mammal being predisposed to that condition comprises administering to the mammal a prophylactically effective amount of the polypeptide of the invention, and a method of treating a mammal afflicted with atherosclerosis comprises the administration of a therapeutically affective amount of the polypeptide disclosed herein.

10 Claims, 1 Drawing Sheet

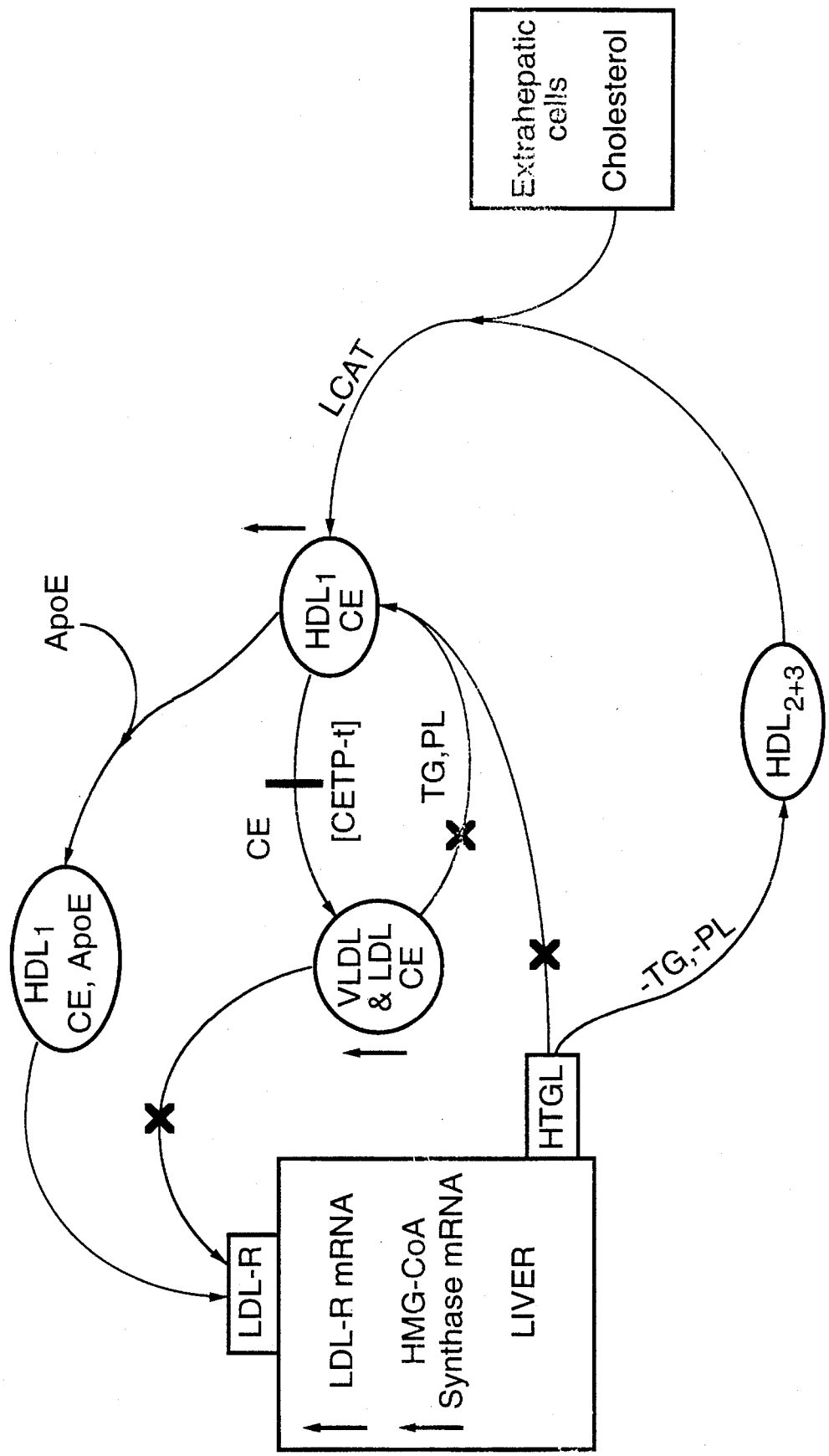

CETP INHIBITOR POLYPEPTIDE, ANTIBODIES AGAINST THE SYNTHETIC POLYPEPTIDE AND PROPHYLACTIC AND THERAPEUTIC ANTI-ATHEROSCLEROSIS TREATMENTS

This is a continuation of application Ser. No. 07/811,049, filed on Dec. 19, 1991 which was abandoned upon the filing hereof.

BACKGROUND OF THE INVENTION

The work leading to the present invention was partially supported by National Heart, Lung and Blood Institute Grants Nos. HL28972 and HL41256, and Contract No. HV53030. The government may hold rights in the present patent.

1. Field of the Invention

This invention relates to an endogenous baboon plasma cholesteryl esters transfer protein (CETP) inhibitor polypeptide. More specifically, this invention relates to the identification and characterization of the polypeptide and to novel synthetic peptides possessing inhibitory activity of CETP. The endogenous inhibitory peptide has a molecular weight of 4000, is present in plasma in the form of modified apo A-I and apo E having molecular weights of 31kD and 41kD, respectively, and has a common amino acid sequence with the N-terminal fragment of apo C-I. This invention also relates to an anti-atherosclerosis composition, a kit, and to antibodies raised against the N-terminal amino acid sequence of the inhibitory polypeptide. The inhibitory peptide of the invention, fragments thereof and analogues thereof are useful for the prophylactic and therapeutic treatment of atherosclerosis.

2. Description of the Background

Atherosclerosis is one of the most widespread health problems in the United States today as are its attendant complications, particularly coronary heart disease. A number of risk factors have been associated with the development of premature atherosclerosis, primarily elevated plasma cholesterol levels. Due to the crucial role cholesterol appears to play in the occurrence of heart disease, a great deal of attention has been devoted to studying its synthesis, transport and metabolism in the human body.

Of particular interest is the establishment of relationships between the levels of plasma lipoproteins or serum lipids and the risk of development of coronary heart disease. Both high density lipoproteins (HDL) and low density lipoproteins (LDL) carry cholesterol mainly in the form of cholesteryl esters (CE). There are some indications, however, that while LDL cholesterol is a positive risk factor, HDL cholesterol is an even more important negative risk factor. Although the exact functions of these lipoproteins have not been completely established, HDL appears to serve for the removal of cholesterol from peripheral cells and its transport back to the liver, where a large proportion of the cholesterol excreted from the body is removed.

LDL and HDL are believed to play key roles in the development of cardiovascular disease by overloading the lysosomes of the walls of arterial cells with metabolites which are generally hydrolyzed slowly, such as CE and triglycerides. These products are evacuated from the liver and intestine by plasma LDL. When the amount of lipids to be transported exceeds the transporting capacity of HDL to the liver for excretion, CE become deposited in the cells in certain critical areas, such as arterial walls. This overloading eventually results in impaired cell function, and if continued may produce cell death. A continuous overloading results in the accumulation of cellular debris and tile formation of atherosclerotic plaque in the vessel wall. This, in turn, leads to the blockage of the affected artery and/or muscular spasm, events which may manifest themselves as coronary heart disease or strokes. Thus, the level of HDL in plasma has been negatively correlated with the probability of developing atherosclerosis in humans and experimental animals.

Although the level of HDL has been shown to vary considerably among individuals, the means of regulation of such plasma level remains to be elucidated.

CETP transfers CE from HDL to VLDL and LDL, and it has been suggested that it plays an important role in the regulation of plasma HDL levels. Some hyperalphalipoproteinemic patients were reported to have high levels of large HDL particles that were clearly separate from LDL. Plasma samples from these patients were shown to lack CETP activity (Koizumi et al, Atherosclerosis 58:175–186(1985)). A homozygous subject with familial hyperalphalipoproteinemia was found to have impaired transfer of CE from HDL to LDL (Yokoyama et al., Artery 14:43–51(1986)). A fraction of density d>1.21 g/ml from the subject's plasma evidenced substantial CETP activity with normal HDL. The HDL, however, proved to be a poor substrate for CETP.

Certain animal sires and their progeny possess unusual lipoproteins patterns, e.g., lipoproteins of a density intermediate to that of LDL and HDL, or large high density lipoproteins. These lipoproteins have been designated $HDL_1$, and the animal phenotype as "high $HDL_1$". Baboon strains possessing, for instance, patterns of either high or low $HDL_1$ are known. In most cases, $HDL_1$ separates either as a distinct peak between LDL and HDL or as a shoulder to the HDL peak, and is induced by a high cholesterol, high lard (HCHF) diet. The proportion of $HDL_1$ diminishes when the baboons are fed a diet that is either enriched ill polyunsaturated fat, with or without cholesterol. Occasionally, however, the amount of $HDL_1$ present in high $HDL_1$ baboons fed the chow diet is low.

In some baboon families, the level of plasma $HDL_1$ was shown to increase when the animals are challenged with a HCHF diet. When fed a HCHF diet, the baboons also show higher plasma HDL. More generally, the accumulation of HDL in baboons as well as in humans is associated with a slower transfer of CE from HDL to very low density lipoproteins (VLDL) and LDL. Thus, baboons with high $HDL_1$ plasma levels are excellent as animal models for the study of hyperalphalipoproteinemia.

In a previous study, some of the present inventors reported that a slower transfer of CE from HDL to VLDL and LDL was observed in high $HDL_1$ baboons. This was attributed to the presence of a CETP protein inhibitor associated with HDL and intermediate density lipoprotein (IDL) particles (Kushwaha et al, J. L. Lipid Res. 31:965–974(1990)). An accumulation of $HDL_1$ in the high $HDL_1$ baboons fed a HCHF diet was reported along with a slower transfer of CE from HDL to LDL. A similar protein was found in human plasma by Son and Zilversmit (Son and Zilversmit, B.B.A. 795:473–480(1984)). The human protein has a molecular weight of 31,000 and suppresses the transfer of triacylglycerol and CE.

Several other species including rat, pig and dog, have been reported to readily accumulate $HDL_1$ in plasma. Kurasawa et al (1985), supra, reported that a homozygous subject with familial hyperalphalipoproteinemia, has impaired CE transfer between HDL and LDL (Kurasawa et al, J. B. Biochem. 98:1499–1508(1985)). Separately, Yokoyama et al reported that a plasma fraction of d>1.21 g/ml of the same subject evidenced substantial CE transfer activity when tested with normal HDL (Yokoyama et al, Artery 14(1):43–51(1986)). The HDL particles accumulated by this subject were substantially larger in molecular size than ordinary $HDL_2$.

HDL is generally divided into subfractions based on their particle sizes and densities. These fractions include $HDL_1$, $HDL_2$ and $HDL_3$. $HDL_1$ has the largest particles and is usually not present in the plasma of normal humans or non-human primates. $HDL_2$ and $HDL_3$ are the normal components of human plasma. $HDL_2$ is larger than $HDL_3$ and differs between men and women.

Many attempts have been made to interfere with the transport and transfer of cholesterol in mammalians in order to alter its plasma levels. Among them are the following.

U.S. Pat. No. 4,987,151 to Taboc discloses triterpene derivatives that inhibit acyl coenzyme A:cholesterol acyltransferase (ACAT) enzyme. The ACAT is a cellular enzyme that is not present in plasma, and esterfies cellular cholesterol to form CE. This enzyme is different from the CE transfer protein (CETP) present in plasma. The CETP does not form CE as does the ACAT enzyme. Instead, the CETP transfers CE amongst different plasma lipoproteins.

U.S. Pat. No. 4,643,988 to Segrest et al discloses amphipathic peptides which are capable of substituting for apo A-I in HDL. Apo A-I is known to stimulate the lecithin cholesterol:acyl transferase (LCAT) enzyme, a plasma enzyme that forms CE in HDL. Plasma CETP, in contradistinction, transfers CE from HDL to VLDL and LDL. The function of the CETP enzyme is, therefore, different from that of the LCAT enzyme, as well. The amino acid sequences of the Segrest et al peptides are, in addition, different from the sequences of the CETP inhibitor of this invention.

SUMMARY OF THE INVENTION

This invention relates to a substantially pure polypeptide having activity inhibitory of CE transfer protein (CETP).

This invention also relates to an anti-atherosclerosis composition, comprising an anti-atherosclerosis effective amount of the polypeptide described above; and a pharmaceutically-acceptable carrier.

In addition, this invention relates to an anti-atherosclerosis kit, comprising in separate containers at least one unit of the composition described above;

at least one syringe; and at least one needle.

This invention also relates to an antibody having specificity for a polypeptide selected from the group consisting of the polypeptide described above;

baboon CETP polypeptide inhibitor;

1–36 amino acid N-terminal fragment of apo C-I;

modified apo A-I (MW:31kD); and modified apo E (MW:41kD).

In a different aspect, this invention relates to a method of preventing atherosclerosis in a mammal being predisposed to that condition, comprising administering to the mammal a prophylactically effective amount of the polypeptide described above.

This invention also relates to a method of treating a mammal afflicted with atherosclerosis comprising administering to the mammal a therapeutically effective amount of the polypeptide described above.

Other objects, advantages and features of the present invention will become apparent to those skilled in the art from the following discussion.

BRIEF DESCRIPTION OF THE DRAWING

A drawing of what is known about the association of cholesterol with the different fractions of lipoproteins in plasma and in the liver is shown in the figure.

The metabolic steps leading to the accumulation (↑) of $HDL_1$, VLDL and LDL are shown above. $HDL_{2+3}$ collects cholesterol from extrahepatic cells, which is then esterified by LCAT to form cholesteryl esters (CE) and stored in the core of the particles. The HDL becomes larger in size ($HDL_1$) and may pick up apo E to attain a particle form which is removed by LDL receptors (LDL-R) on liver cells. The CE enriched $HDL_1$ may also donate CE to VLDL and LDL. This is mediated by CETP. Due to the presence of a CETP inhibitor, such as the one provided herein, CE transfer is slow (bar) and the reciprocal transfer of triglycerides (TG) does not take place (X). The triglyceride-poor HDL is thus not a suitable substrate for hepatic triglyceride lipase (HTGL). Due to the presence of the CETP inhibitor, in plasma, VLDL and LDL are thus not available to the liver. As a consequence of this, the liver then increases the expression of messages for the increased production of LDL receptor and 3 hydroxy, methyl, glutaryl-coenzyme A (HMG-COA) synthase.

The increase in LDL receptor in the liver leads to an increase in uptake of LDL or HDL, with apo E, and consequently, to a greater delivery of cholesterol to the liver. An increase in synthesis of HMG-CoA synthase leads to an increase in synthesis of cholesterol in the liver to meet all cellular needs. Thus, the presence of a CETP inhibitor in plasma will prevent the uptake of VLDL and/or LDL by tissues as well as the deposition of cholesteryl esters.

DESCRIPTION OF THE PREFERRED EMBODIMENT

This invention arose by the desire of the inventors to provide and unobvious approach to the prevention and treatment of atherosclerosis in humans.

In general, high levels of HDL have an anti-atherogenic effect whereas high levels of LDL have an atherogenic effect. The circulation in blood of compounds, such as cholesterol, that are insoluble in water requires the formation of particles. The insoluble components, e.g., cholesteryl esters and triglycerides, are packed in the core of the particles and surrounded by polar components such as proteins, phospholipids and the like. These particles are called lipoproteins, and have, thus, an outer polar shell and a non-polar core. These associations of lipoproteins containing CE in the core and, depending on their sizes and densities, have been named VLDL, IDL, LDL, and HDL.

VLDL is the largest lipoprotein secreted by the liver and is converted into IDL, and then to LDL, after the triglycerides contained by the VLDL are hydrolyzed by the lipoprotein lipase enzyme present on the surface of the arterial walls. LDL is the major lipoprotein that provides cholesteryl ester to extrahepatic and hepatic tissues. HDL is also secreted by the liver and is divided in $HDL_2$ and $HDL_3$ on the basis of size and density. A function of HDL is to pick up cholesterol from extrahepatic cells and deliver it to the liver, either through VLDL and LDL or through large HDL which is enriched with apo E. These large HDL particles are called $HDL_1$ and they do not stay in the plasma for long periods of time. They are rapidly removed by the liver or converted back to $HDL_2$ after donating their cholesteryl esters to VLDL and LDL.

$HDL_1$ is not present in either normal humans or non-human primates. As indicated above, $HDL_1$ appears as a distinct band in the plasma of baboons that have been fed a HCHF diet. From what is known, when cholesterol enters the blood stream it becomes associated with HDL in the form of a CE, with the help of the LCAT enzyme. In HCHF-fed baboons, this appears as an $HDL_1$-CE fraction. The CE is then transferred from HDL to VLDL and LDL to form VLDL-CE and LDL-CE with the aid of the CETP enzyme. These particles then enter the liver cells through the LDL receptor (LDL-R). After being metabolized in the liver cells, the VLDL-CE is returned to the plasma and thus to the periphery of the mammalian body, where its deposition may occur leading to atherosclerosis.

An inhibitor of CETP, such as the one provided by this invention, blocks the transfer of CE from HDL to VLDL and LDL. Instead, a shunt is favored that leads to the association of the CE with apo E and to the formation of $HDL_1$-CE-apo E particles that can enter the liver cells through the LDL receptor (LDL-R).

The apolipoprotein C-I of various species but not baboon, are known. The Apo C-I is a single polypeptide of molecular weight 6600, consisting of 57 amino acids. It is a basic protein that is mainly present in VLDL and HDL, with HDL serving as a reservoir for this protein. LDL, on the other hand, contains little apo C-I. It has recently been shown that apo C-I displaces apo E from VLDL and affects its binding to the LDL receptor.

The polypeptide inhibitor of CETP that is described herein has a common sequence with the N-terminal fragment of apo C-I. This fragment includes at least 36 amino acids as shown below.

The endogenous polypeptide provided by this invention has a molecular weight of about 4,000 and becomes associated or binds to apo A-I and apo E in plasma. Its N-terminal 36 amino acids are shown below.

A polypeptide having the sequence corresponding to amino acids 1 to 36 of the above sequence was synthesized by the inventors and shown to be inhibitory of CETP in vitro. The peptide has the following sequence.

(SEQ. ID. NO: 1)
1   2   3   4   5   6   7   8   9   10  11
Asp—Val—Ser—Ser—Ala—Leu—Asp—Lys—Leu—Lys—Glu—

12  13  14  15  16  17  18  19  20  21  22
Phe—Gly—Asn—Thr—Leu—Glu—Asp—Lys—Ala—Trp—Glu—

23  24  25  26  27  28  29  30  31  32  33
Val—Ile—Asn—Arg—Ile—Lys—Gln—Ser—Glu—Phe—Pro—

34  35  36
Ala—Lys—Thr.

Fragments of that polypeptide comprising the C-terminal fragments of amino acids 28 to 36 and amino acids 16 to 36 showed limited inhibitory activity of CETP at 50 µg. However, the fragment comprising the C-terminal amino acids 28 to 36 showed at 200 µg an activity inhibitory of CETP approximately the same as that of the 36 amino acid peptide. The N-terminal fragments comprising amino acids 1 to 15, amino acids 1 to 20 and amino acids 1 to 10, as well as tile intermediate fragments comprising amino acids 15 to 30 and the like, corresponding to the synthesized peptide have been shown active as inhibitors of CETP.

Analogues of the polypeptide of the invention and fragments thereof having inhibitory activity of CETP are also part of the invention. The analogues may have one or more substitutions in their sequences while still preserving their inhibitory activity. Examples of analogues suitable as inhibitors of CETP are analogues of the peptide of the invention and fragments thereof, such as those where one or more of the amino acids are substituted in accordance with the guidelines provided below.

The substitute amino acids may be selected from the group consisting of

Glu, $C_\alpha$-methylAsp, and β-carboxyAsp for Asp;

isoVal, norVal, Leu, and $C_\alpha$-methylVal for Val;

Gly, β-Ala, $C_\alpha$-methylAla, and 2-amino butyric acid for Ala;

norLeu, isoLeu, and $C_\alpha$-methylLeu for Leu;

ornithine, Arg, citrulline and $C_\alpha$-methylLys for Lys;

Ala and 2-amino isobutyric acid for Gly;

Gln, citrulline, and $C_\alpha$-methyl Trp for Trp;

2-amino adipic acid, Asp, and $C_\alpha$-methylGlu for Glu;

Leu, norLeu, and $C_\alpha$-methylIle for Ile;

Lys, homoArg, citrulline and $C_\alpha$-methylArg for Arg;

Asn, citrulline, and $C-_\alpha$-methylGln for Gln;

2-amino-4-phenylbutyric acid, and $C_\alpha$-methylPhe for Phe;

Ser and $C_\alpha$-methylThr for Thr;

Thr and $C_\alpha$-methylSer for Ser; and 3,4-dehydroPro and $C_\alpha$-methylPro for Pro; and combinations thereof.

However, other substituents of a nature equivalent to that of the substituted amino acid as is known in the art may also be utilized, alone or in combination with other substituents.

It is therefore provided in accordance with this invention, a substantially pure polypeptide having activity inhibitory of CETP.

In one embodiment of the invention, the polypeptide is capable of inhibiting the binding of an about 31kD modified apo A-I polypeptide present in the plasma of high $HDL_1$ baboons or a peptide of the sequence (SEQ. ID. NO. 1)
1   2   3   4   5   6   7   8   9   10  11
Asp—Val—Ser—Ser—Ala—Leu—Asp—Lys—Leu—Lys—Glu—

12  13  14  15  16  17  18  19  20  21  22
Phe—Gly—Asn—Thr—Leu—Glu—Asp—Lys—Ala—Trp—Glu—

23  24  25  26  27  28  29  30  31  32  33
Val—Ile—Asn—Arg—Ile—Lys—Gln—Ser—Glu—Phe—Pro—

34  35  36
Ala—Lys—Thr, to an antibody raised against the above peptide.

In another embodiment, the polypeptide of the invention is capable of inhibiting the binding of an about 4kD CETP inhibitor polypeptide present in the plasma of high $HDL_1$ baboons to an antibody raised against a peptide of the formula (SEQ. ID. NO. 1)
1   2   3   4   5   6   7   8   9   10  11
Asp—Val—Ser—Ser—Ala—Leu—Asp—Lys—Leu—Lys—Glu—

12  13  14  15  16  17  18  19  20  21  22
Phe—Gly—Asn—Thr—Leu—Glu—Asp—Lys—Ala—Trp—Glu—

```
23   24   25   26   27   28   29   30   31   32   33
Val—Ile—Asn—Arg—Ile—Lys—Gln—Ser—Glu—Phe—Pro—

34   35   36
Ala—Lys—Thr.
```

In still another embodiment, the polypeptide of this invention is capable of inhibiting the binding of an about 41 kD modified apo E polypeptide present in the plasma of high $HDL_1$ baboons with antibody raised against the 36 amino acid N-terminal fragment of apo C-I or a peptide of the formula

```
                                                    (SEQ. ID. NO. 1)
1    2    3    4    5    6    7    8    9    10   11
Asp—Val—Ser—Ser—Ala—Leu—Asp—Lys—Leu—Lys—Glu—

12   13   14   15   16   17   18   19   20   21   22
Phe—Gly—Asn—Thr—Leu—Glu—Asp—Lys—Ala—Trp—Glu—

23   24   25   26   27   28   29   30   31   32   33
Val—Ile—Asn—Arg—Ile—Lys—Gln—Ser—Glu—Phe—Pro—

34   35   36
Ala—Lys—Thr.
```

In still another embodiment, the polypeptide is capable of inhibiting the binding of the 36 amino acid N-terminal fragment of apo C-I or a peptide of the formula

```
                                                    (SEQ. ID. NO. 1)
1    2    3    4    5    6    7    8    9    10   11
Asp—Val—Ser—Ser—Ala—Leu—Asp—Lys—Leu—Lys—Glu—

12   13   14   15   16   17   18   19   20   21   22
Phe—Gly—Asn—Thr—Leu—Glu—Asp—Lys—Ala—Trp—Glu—

23   24   25   26   27   28   29   30   31   32   33
Val—Ile—Asn—Arg—Ile—Lys—Gln—Ser—Glu—Phe—Pro—

34   35   36
Ala—Lys—Thr,
``` with an antibody raised against modified apo A-I.

Preferred polypeptides are the polypeptide of the sequence

```
                                                    (SEQ. ID. NO. 1)
1    2    3    4    5    6    7    8    9    10   11
Asp—Val—Ser—Ser—Ala—Leu—Asp—Lys—Leu—Lys—Glu—

12   13   14   15   16   17   18   19   20   21   22
Phe—Gly—Asn—Thr—Leu—Glu—Asp—Lys—Ala—Trp—Glu—

23   24   25   26   27   28   29   30   31   32   33
Val—Ile—Asn—Arg—Ile—Lys—Gln—Ser—Glu—Phe—Pro—

34   35   36
Ala—Lys—Thr,
``` anti-4kD peptide antibody-binding inhibitory fragments hereof; and anti-4kD peptide antibody-binding inhibitory analogues thereof having at least one substitute amino acid selected from the group consisting of Glu, $C_{60}$-methylAsp, and β-carboxy Asp for Asp;
isoVal, norVal, Leu, and $C_\alpha$-methylVal for Val;

Gly, β-Ala, $C_\alpha$-methylAla, and 2-amino butyric acid for Ala;

norLeu, isoLeu, and $C_\alpha$-methylLeu for Leu;

ornithine, Arg, citrulline and $C_\alpha$-methylLys for Lys;

Ala and 2-amino isobutyric acid for Gly;

Gln, citrulline, and $C_\alpha$-methyl Trp for Trp;

2-amino adipic acid, Asp, and $C_\alpha$-methylGlu for Glu;

2-amino adipic acid, Asp, and $C_\alpha$-methylTrp for Trp;

Leu, norLeu, and $C_\alpha$-methylIle for Ile;

Lys homoArg, citrulline and $C_\alpha$-methylArg for Arg;

Asn, citrulline, and $C_\alpha$-methylGin for Gln;

2-amino-4-phenylbutyric acid and $C_\alpha$-methylPhe for Phe;

Ser and $C_\alpha$-methylThr for Thr;

Thr and $c_\alpha$-methylSer for Ser;

3,4-dehydroPro and $C_\alpha$-methylPro for Pro; and combinations thereof.

In one particularly preferred embodiment, the polypeptide contains amino acids 1 through 36 of the above sequence. In still another particularly preferred embodiment, the peptide is selected from the group consisting of peptide fragments comprising amino acids 1 to 17, 1 to 20 and 1 to 25, and fragments thereof having anti- 4kD peptide antibody/1–36 amino acid peptide binding inhibitory activity.

In still another preferred embodiment, the peptide fragments are selected from the group consisting of peptides comprising amino acids 1 to 18, and 1 to 28, and fragments thereof having anti-4kD peptide antibody/1–36 amino acid peptide binding inhibitory activity.

Also preferred are analogues with the Lys, Asp and Asn amino acids substituting for the Arg, Glu and Gln amino acids; the Ser, Leu, and Ala amino acids substituting for the Thr, Ile and Gly amino acids; the ornithine, citrulline and αaminoadipic acid amino acids substituting for the Lys and Glu amino acids.

Also preferred are the following analogues. Peptides comprising amino acid sequences where amide bond(s) (e.g., —C(O)—NH—) linking any pair, and up to all pairs, of amino acids comprising amino acids 1 to 17, 1 to 20, 1 to 25, 1 to 36, and fragments thereof having anti-4kD peptide antibody/1–36 amino acid peptide binding inhibitory activity are replaced by thioether bonds (e.g., $—CH_2—S—$), alkyl such as ethyl ($—CH_2—CH_2—$), and/or amino (e.g., $—CH_2—NH_2$) linkages. These analogues may be purchased commercially or prepared by methods known to those skilled in the art as long as the antibody 1–36 amino acid peptide binding and CETP inhibitory activities of the peptides (analogues) are retained to some degree.

However, other analogues are also part of this invention as long as they preserve the inhibitory activity of the antibody/1–36 amino acid peptide binding.

The CETP inhibitory polypeptide of the invention may be provided as a powder, preferably in freeze-dried form, as a solution, preferably frozen at below −20° C., and the like, to prevent proteolysis.

This invention also provides an anti-atherosclerosis composition, comprising an anti-atherosclerosis effective amount of the polypeptide of the invention; and a pharmaceutically-acceptable carrier.

When the composition is used as a preventative tool, it may contain 10 to 200 mg and more preferably 20 to 100 mg of the polypeptide. However, other amounts are also suitable. When the composition is intended for therapeutic use, the amount of polypeptide present is preferably about 10 to 400 mg, and more preferably about 20 to 300 mg. However, other amounts may also be utilized.

Any and all pharmaceutically-acceptable carriers known in the art for administration of peptides to mammals, and preferably to humans, are suitable for use herein. These are known in the art and need not be further described herein. Examples, however, are saline, human serum albumin and starch. However, others may also be utilized.

The composition of this invention may be provided in unit form, preferably in a sterile, closed container, and more preferably in a sealed container.

A kit, comprising in separate containers as least one unit of the anti-atherosclerosis composition of tile invention;

at least one syringe; and at least one needle.

Typically, a kit may contain from about 1 to 20 units of the composition of the invention, but could contain 50 units or more. In addition, the kit may contain 1 to 20, but and sometimes 50 or more syringes if they are disposable, and 1 to 20, but sometimes up to 50 or more needles if they are disposable. The components of the kit are provided in a sterile form, be it wrapped in a sealed, sterilized wrapping, or in some other way. If not disposable, the syringe and needle may be autoclaved between uses.

The composition of tile invention is preferably administered intravenously, although it may also be administered intraperitoneally, subcutaneously or intramuscularly.

The composition may preferably have a pH of about 7 to 9, and more preferably about 8 to 9, which may be adjusted with the addition of a base, acid or buffer as is known in the art.

This invention also provides an antibody having specificity for a polypeptide selected from the group consisting of the polypeptide of the invention;

the baboon CETP polypeptide inhibitor, fragments thereof and analogues thereof;

the 1–36 amino acid N-terminal fragment of apo C-I;

modified apo A-I (MW:31kD); and modified apo E (MW:41kD).

The antibodies of the invention may be raised in mammals as is known in tile art. (Albers, J. J., Hazzerd, W. R., "Immunochemical Quantification of the Human Lp(a) Lipoprotein", Lipids 9:15–26(1974)).

Typically, tile antibodies may be raised in rabbit, goat, sheep, pig and chicken. However, other mammals may also be utilized. Preferred are rabbit antibodies. Also preferred are polyclonal antibodies. However, monoclonal antibodies may also be prepared by methods known in the art (Kohler, G., and Milstein, D., "Continuous Cultures of Fused Cells Secreting Antibody of Predefined Specificity", Nature (London) 256:495–497(1975)).

In one preferred embodiment, the antibody of the invention is capable of specifically binding to modified apo A-I.

In another preferred embodiment, the antibody is capable of specifically binding to the baboon CETP inhibitor polypeptide of this invention.

In still another embodiment, the antibody of the invention is capable of specifically binding to the polypeptide of the sequence (SEQ. ID. NO. 1)

| 1 | 2 | 3 | 4 | 5 | 6 | 7 | 8 | 9 | 10 | 11 |
|---|---|---|---|---|---|---|---|---|----|----|
| Asp | Val | Ser | Ser | Ala | Leu | Asp | Lys | Leu | Lys | Glu |

| 12 | 13 | 14 | 15 | 16 | 17 | 18 | 19 | 20 | 21 | 22 |
|----|----|----|----|----|----|----|----|----|----|----|
| Phe | Gly | Asn | Thr | Leu | Glu | Asp | Lys | Ala | Trp | Glu |

| 23 | 24 | 25 | 26 | 27 | 28 | 29 | 30 | 31 | 32 | 33 |
|----|----|----|----|----|----|----|----|----|----|----|
| Val | Ile | Asn | Arg | Ile | Lys | Gln | Ser | Glu | Phe | Pro |

| 34 | 35 | 36 |
|----|----|----|
| Ala | Lys | Thr | fragments thereof and analogues thereof as described above.

In still another preferred embodiment of the invention, the antibody is capable of specifically binding to modified apo E.

The antibody of the invention, in another preferred embodiment is also capable of specifically binding to apo C-I, and more preferably to the 1–36 N-terminal fragment thereof.

In another aspect of the invention, a method is provided for preventing atherosclerosis in a mammal being predisposed to that condition. The method comprises administering to the mammal a prophylactically effective amount of the polypeptide of the invention, or of the anti-atherosclerosis composition described above.

In a preferred embodiment, the polypeptide is administered in an amount of about 10 to 200 mg, and preferably about 2 to 100 mg for preventative applications. However, other amounts may also be administered. The polypeptide or composition thereof may be administered in a small volume of carrier, e.g., 0.2 to 1.5 ml of saline or other carriers, as is known in the art.

The polypeptide of the invention may be administered intravenously, to a fragment of the population, particularly the human population, that is not afflicted by high blood cholesterol and hyperbetalipoproteinemia, but, as determined by other means, may be at risk of being afflicted by atherosclerosis. One such example may be a familial trait having been determined.

The polypeptide of this invention may be administered on a daily basis, or at longer intervals if provided as a slow release composition as is known in the art, such as depoestradiol provided by the UpJohn Co. (UpJohn Co., Kalamazoo, Mich.).

In another aspect, the present invention provides a method of treating a mammal afflicted with atherosclerosis. The method comprises administering to the mammal a therapeutically affective amount of the polypeptide of the invention. When administered for therapeutic purposes, the polypeptide may be injected in an amount of about 10 to 400 mg, and more preferably 20 to 300 mg. However, other amounts as assessed by a practitioner in specific cases, may also be administered.

In this case, as in the case of the prophylactic administration, the polypeptide may be administered intravenously, among other routes.

Having now generally described this invention, the same will be better understood by reference to certain specific examples, which are included herein for purposes of illustration only and are not intended to limiting of the invention or any embodiment thereof, unless so specified.

EXAMPLES

Example 1: Animals and Diet

Adult male and female baboons (papio sp.) held in a baboon colony at the Southwest Foundation for Biomedical Research in San Antonio, Texas, were used as blood donors for these studies. Among these, 24 baboons had a high $HDL_1$ phenotype and 32 had a low $HDL_1$ phenotype (Williams, M. C., et al, "Detection of abnormal lipoprotein in a large colony of pedigreed baboons using high-performance gel exclusion chromatography", J. Chromat. 308:101–109(1984)).

Half of the high $HDL_1$ baboons (n=16) were maintained on a HCHF diet, the composition of which has been previously described (Kushwaha, R. S., et al, "Metabolism of apolipoprotein B. in baboons with low and high levels of low density lipoproteins", J. Lipid Res. 27:497–507(1986)).

Most of the baboon donors of the low $HDL_1$ phenotype were maintained on a chow diet (Purina Monkey Chow, manufactured by Ralston Purina Co., St. Louis, Mo.). The monkey chow is low in fat (10% of total calories) and high in carbohydrate (62% of total calories). In addition, the chow has a very low cholesterol content (0.03 mg/Kcal).

The high HDL$_1$ baboons were progeny of two sires (X1672 and X102) who had a high HDL$_1$ phenotype. The low HDL$_1$ baboons were progeny of a number of sires who did not have a high HDL$_1$ phenotype. The presence of HDL$_1$ was detected by high performance liquid chromatography (HPLC) as described previously (Williams et al "Detection of abnormal lipoprotein in a large colony of pedigreed baboons using high-performance gel exclusion chromatography", J. Chromatography 308:101–109(1984)).

Example 2: Preparation of $^3$H Cholesteryl Ester HDL

High and low HDL$_1$ baboons were immobilized with 10 mg/kg of ketamine HCl and bled. The blood was collected in tubes containing 1 mg/ml EDTA, and plasma separated by low speed centrifugation at 6° C. The plasma was treated with sodium azide, chloramphenicol, gentamycin sulfate, phenylmethyl-sulfonyl fluoride and DTNB as described previously (Kushwaha, R. S., et al, "Impaired plasma CE transfer with accumulation of larger high density lipoproteins in some families of baboons (Papio sp.)," J. Lipid Res. 31:965–973(1990)).

20 to 60 µCi of tritiated cholesteryl linoleate were dissolved in ethanol and then added to the plasma. The plasma was flushed with nitrogen and incubated for 20 hrs at 4° C.

After incubation, HDL$_3$ was isolated by density gradient ultracentrifugation (McGill, H. C., et al, "Dietary effects on serum lipoproteins of dyslipoproteinemic baboons with high HDL$_1$", Arteriosclerosis 6:651–663(1986); Redgrave, T. G., et al, "Separation of plasma lipoproteins by density-gradient ultracentrifugation", Anal.Biochem. 65:42–49(1975)), dialyzed against saline/EDTA, and used as a substrate for the CE transfer reaction.

The total and free cholesterol contents of HDL$_3$ were measured prior to use in the assay.

Example 3: Preparation of Acceptor Lipoproteins and CETP Source

VLDL+LDL from low HDL$_1$ baboons was used as the acceptor of CE from HDL$_3$. A VLDL+LDL fraction of d<1.040 g/ml was isolated from 100–200 ml of blood by sequential ultracentrifugation as described previously (Kushwaha et al (1986), supra). Total and free cholesterol contents in acceptor lipoproteins were measured by enzymatic methods (Wako Pure Chemical Co.) (Allain, C. C., et al., *"Enzymatic Determination of Total Serum Cholesterol"*, Clin. Chem. 20:470–475(1974).

After separation of VLDL+LDL, the bottom fraction was adjusted to d=1.21 g/ml by adding solid KBr, and total lipoproteins were isolated by ultracentrifugation (Kushwaha et al (1986), supra). The bottom fraction of d>1.21 g/ml was also collected.

All lipoprotein fractions and the lipoprotein-deficient fraction of d>1.21 g/ml (LPDS) were dialyzed against saline/EDTA. The LPDS was used as the source of CETP.

Example 4: Cholesteryl Ester Transfer Assay

The CE transfer activity of a sample was assayed by a modification of a procedure described previously (Kushwaha et al, (1986), supra).

Briefly, $^3$H CE-labeled HDL$_3$ containing 50–100 µg of CE from low HDL$_1$ baboons was incubated with VLDL+LDL containing 100–300 µg CE in the presence of LPDS. The acceptor lipoproteins and the LPDS were obtained from low HDL$_1$ baboon plasma (chow diet). In some cases the HDL$_3$ was obtained from high HDL$_1$ baboons maintained on the HCHF diet.

The incubations were carried out at 4° C. (control) and 37° C. for 4–6 hrs, and terminated by placing the samples on ice. The assay mixture was then ultracentrifuged to separate VLDL+LDL having a d>1.040 g/ml, and the radioactivity in the lipoproteins was counted as described previously (Kushwaha et al, (1986), supra). Any difference observed in the radioactivity transferred from HDL to VLDL+LDL at 4° C. and 37° C. was attributed to CETP activity in the LPDS.

Time course experiments gave a linear response up to 7 hrs. Similarly, the CETP activity was linear with increasing LPDS, up to 140 µl LPDS, which was derived from an equivalent volume of plasma.

The polypeptide of the invention, and synthetic fragments thereof were added to the reaction mixture to determine their CETP inhibitory activities, along with an appropriate synthetic control peptide.

The percent difference between the control experiment and the assay with inhibitor peptide was expressed as the inhibitor activity.

Example 5: Identification of Inhibitor Polypeptide

The bottom non-lipoprotein fraction obtained by ultracentrifugation for 72 hrs was analyzed for protein content by 10% SDS-polyacrylamide gel electrophoresis (Laemmli, U. K., "Cleavage of structural proteins during the assembly of the head of bacteriophage T4", Nature 227:680–685(1970)), without β-mercaptoethanol pretreatment.

To determine differences in small molecular weight apolipoproteins, delipidated lipoproteins of d<1.21 g/ml from high and low HDL$_1$ baboons were separated by 15–19% SDS-polyacrylamide gel electrophoresis with β-mercaptoethanol pretreatment prior to loading the samples onto the gels.

Example 6: Electroelution of Inhibitor Polypeptide

The lipoproteins fraction of d<1.21 g/ml from high HDL$_1$ baboon plasma was delipidated with ether:ethanol (Floren, C. H., et al, "Estrogen-induced increase in uptake of cholesterol-rich very low density lipoproteins in perfused rabbit liver", Metabolism 30:367–374(1981)), and separated by 15% SDS gel electrophoresis (Laemmli, (1970), supra) after addition of β-mercaptoethanol. A small molecular weight protein band was cut and transferred onto a tube gel (15%).

A dialysis tube of molecular weight cut-off point 1000 was attached to the bottom of the gel tube to receive the electroeluted peptide. The thus electroeluted peptide was dialyzed and quantitated by comparing its absorbance at 660 nm with a known amount of stained albumin electroeluted at the same time.

Example 7: Antibody Preparation

The apolipoproteins were separated by 15% SDS-gel electrophoresis and stained (Laemmli, (1970), supra). The stained bands were transferred onto a nitrocellulose membrane. The bands corresponding to the inhibitor polypeptide were cut out (0.05 mg) and dissolved in 0.5 ml of filtered DMSO. 0.5 ml Freund's adjuvant were then added and thoroughly mixed and the mixture was injected intradermally into two rabbits. After 30 days, the rabbits were boosted with a similar amount of electroeluted protein band. Antibody titer was measured by Western blotting. The rabbits were boosted again 3 times.

For the preparation of antibody against the synthetic polypeptide, 500 µg of polypeptide were dissolved in 400 µl of titer max (CytRx Corporation, Atlanta, Ga.), and injected into rabbits intradermally. The rabbits were boosted with 500 µg of the synthetic peptide in 200 µl of Titer Max on the 28th day. The serum was tested on the 42nd day. The rabbits were bled and anti-serum was obtained as needed.

Example 8: Immunoaffinity Chromatography

An immunoaffinity column was prepared using CnBr-activated Sepharose beads (Pharmacia Co.). The bound ligand was IgG precipitated from the serum of rabbits having antibodies. The method used to precipitate IgG was similar to that described by McKinney and Parkinson (McKinney, M. M. and Parkinson, A., "A simple, non-chromatographic procedure to purify immunoglobins from serum and ascites fluid", J. Immunological Methods, 96:271–278(1987)).

Briefly, 5 ml of rabbit serum were diluted 4-fold with acetate buffer, pH 4.0. 625 µl of caprylic acid were added dropwise to precipitate albumin and non-IgG proteins. The insoluble materials were removed by centrifugation at 10,000 xg for 30 min. The supernatant was mixed with phosphate buffered saline, and the pH adjusted to 7.4 with 1N sodium hydroxide. The solution was cooled to 4° C. and ammonium sulfate was added to give a final concentration of 45% to precipitate the IgG.

The precipitate was recovered as a pellet after centrifugation, and resuspended in phosphate buffered saline. The IgG was dialyzed overnight in 100 volumes of phosphate buffered saline, and then dissolved in sodium acetate buffer, pH 8.3, coupled to 3 g of CnBr-activated Sepharose beads, and maintained in Tris-saline, pH 7.4, until ready to use.

8 ml of plasma were incubated overnight with IgG coupled beads in Tris-saline buffer with gentle rotation. The column was then washed with Tris-saline coupling buffer and sodium acetate buffer as described by Cheung and Albers (Cheung, M. C., and Albers, "Distribution of high density lipoprotein particles with different apolipoprotein composition: particles with A-I and A-II and particles with A-I but no A-II", J. Lipid Res. 23:747–753(1982)).

The bound proteins were eluted with 0.1M acetic acid, pH 3.0, and 1 ml aliquots were collected and read at 280 nm to visualize the peak. The protein fraction was dialyzed immediately against phosphate buffered saline and separated by electrophoresis in 15% SDS-polyacrylamide gels.

Example 9: Inununoblotting

The proteins separated with SDS-polyacrylamide gels were transferred onto Immobilon-P sheets (Millipore, Bedford, Mass.). The sheets were incubated with antibody against inhibitor peptides after blocking of nonspecific sites. The sheets were washed and incubated again with a secondary antibody containing horseradish peroxidase. The addition of boric acid buffer containing 3-amino-9-ethylcarbazole, methanol and hydrogen peroxide produced a coloration.

Example 10: Amino Acid Analysis and Sequencing

Stained bands of proteins were transferred onto Immobilon-P sheets. Selected bands were cut out and hydrolyzed with 50% propionic acid, 50% 12N HCl for 2 hrs at 135° C. Amino acid analysis of each sample was performed using a model 6300 amino acid analyzer (Beckman Co, Palo Alto, Calif.) provided with System Gold software.

The same bands were sequenced using a model 477 A protein sequencer (Applied Biosystems, Foster City, Calif.).

Example 11: Preparation of Synthetic Peptides

The peptides were synthesized by solid-phase peptide synthesis as described by Barany and Merrifield (Barany, G., and Merrifield, R. B., "The Peptides", Analysis, Synthesis, Biology, Gross, E. and Meienhofer, J., eds., vol 2, Academic Press, New York, pp. 1–284(1980)).

The 1–36 amino acid synthetic peptide was assembled from the C-terminus towards tile N-terminus, with the α-carboxyl group of the amino acid attached to a solid support and was then characterized by HPLC.

Example 12: Data Analysis

The values provided in the following examples are averages and are provided as mean±standard error. These values were compared using variance analysis and, if significant differences were detected, the values were compared using Duncan's Multiple Range Test (Duncan, D. B., "Multiple Range and Multiple F Tests", Biometrics 11: 1–12(1955)).

Example 13: Characterization of Proteins from Infranatant Fraction

The CETP inhibitory activity was lost from the HDL when the lipoproteins were extensively ultracentrifuged, e.g., for 72 hrs, or by repeated ultracentrifugation. After ultracentrifugation, the inhibitory activity was found in the infranatant fraction.

To characterize the proteins, the infranatant fraction (d<1.21 g/ml) was separated by 10% SDS polyacrylamide gel electrophoresis in the absence of β-mercaptoethanol.

The infranatant fraction from high $HDL_1$ baboons contained albumin, a protein slightly larger than apo A-I and another protein larger than apo E. Lanes A and B show nonlipoprotein fractions from high and low $HDL_1$ baboons, respectively. The protein bands 1, 3, and 5 correspond to albumin, apo E and apo A-I, respectively. The protein bands 2 and 4 of molecular weights between 1 and 3, and 3 and 5, respectively, correspond to proteins with molecular weights of 41,000 and 31,000, respectively. Protein samples from high $HDL_1$ baboons show only bands corresponding to albumin, a protein of molecular weight 41,000, and a protein of molecular weight 31,000. The molecular weights were determined with standard proteins separated on similar gels (gel picture not shown).

The infranatant fraction from low $HDL_1$ baboons contains these proteins as well, but in addition, it also contains apo A-I and apo E. Both proteins in the apo A-I region were identified by immunoblotting with antibody to apo A-I.

Similarly, both proteins in the apo E region were identified by immunoblotting with antibody to apo E. The molecular weights of the proteins detected by immunoblotting with apo A-I and apo E show a difference of about 4 kD (picture not shown). The estimated molecular weight of apo A-I is about 27,500 and that of the modified apo A-I is about 31,000. Similarly, the estimated molecular weight of apo E is about 37,000 and that of modified apo E is about 41,000. Both apo A-I and apo E are modified by a protein of about 4,000 molecular weight.

Example 14: Detection of CETP Inhibitor Peptide in Plasma of High $HDL_1$ Baboons To determine if a common polypeptide of molecular weight 4,000 was modifying both apo A-I and apo E, plasma lipoproteins of d<1.21 g/ml were separated from high and low $HDL_1$ baboons by 18% SDS-polyacrylamide gel electrophoresis with β-mercaptoethanol.

A higher amount of a 4kD protein was detected in lipoprotein from high $HDL_1$ baboons as compared to lipoprotein from low $HDL_1$ baboons (gel picture not shown).

To determine if the 4kD polypeptide inhibits CE transfer, the polypeptide and albumin were electrolured from the gels, and used ill increasing concentrations in a CE transfer assay mixture with lipoproteins from low $HDL_1$ baboons as described in Example 4 above. Albumin had no effect on the transfer of CE from HDL to VLDL+LDL. The 4kD polypeptide, on the other hand, significantly inhibited CETP activity. (Results are not shown).

Example 15: Characterization of Polypeptide by Affinity Chromatography

Rabbit antibody was prepared against the 4kD polypeptide isolated from lipoproteins obtained from high $HDL_1$ baboons. This antibody was used to prepare an immunoaffinity column. The lipoproteins of d<1.21 g/ml were passed over the immunoaffinity column. The bound lipoproteins eluted with 0.1M acetic acid and separated in 15% SDS-polyacrylamide reducing gels. 4kD, and 31kD polypeptides, and a minor band corresponding to a 41 kD polypeptide were detected.

The column bound peptides (100 µg) inhibited by 31.3+ 1.4% the transfer of CE (mean±SE, n=3) in the CETP assay from low $HDL_1$ baboons.

On the other hand, the addition of IgG to the assay from high $HDL_1$ baboons increased CE transfer by 44.3± 1.5% (n=3), but had no effect on CE transfer from low $HDL_1$ baboons.

Example 16: Comparison of 4kD Inhibitor Polypeptide with Sequence Data Bank

The sequence of this polypeptide was compared to sequences of known proteins using Sequence Data Bank (Reardon, W. R. and Lipmarl, D. J., PNAS (USA) 85:2444–2448(1988)), and was found to have 100% homology with human and crab-eating macaque apo C-I.

The sequence was then compared with apo C-I from baboons and found to be 100% homologous (private communication from Dr. Hixson of the Southwest Foundation for Biomedical Research).

Example 17: Characterization of Inhibitor Polypeptide with Synthetic Peptides

Based on its molecular weight, it was determined that the 4kD inhibitor polypeptide contained approximately 36 amino acids.

Three peptides were synthesized beginning from the C-terminal end of the apo C-I sequence. The first peptide contained 9 amino acids, the second peptide contained 21 amino acids and the third peptide contained 36 amino acids. The 36 amino acid peptide had an amino acid sequence similar to the 4,000 MW polypeptide, the other two were fragments of the synthetic peptide starting from its C-terminus.

50 µg of these peptides were used in a CETP assay with lipoproteins of low $HDL_1$ baboons as described in Example 4 above. A soluble helical peptide with a 1,900 molecular weight utilized as control. The 36 amino acid polypeptide significantly (p<0.01) inhibited CE transfer from HDL to VLDL and LDL, while tile others, including the control peptide, did not.

Example 18: Antibody Against 36 Amino Acid Inhibitor Peptide

Antibody against the 36 amino acid inhibitor peptide was prepared in rabbits as described in Example 7, and used for immunoblotting. The thus prepared antibody recognized the 4kD peptide as well as a 31kD polypeptide from lipoproteins of high $HDL_1$ baboons.

To determine if both the apo C-I and the 4kD polypeptide were present in the plasma of high and low $HDL_1$ baboons, lipoproteins from both phenotypes were separated by 10% SDS gel electrophoresis and immuno-blotted. Two protein bands were detected with the antibody by immunoblotting of samples from high $HDL_1$ baboons. Only a single band was detected in samples from low $HDL_1$ baboons.

In addition, isoelectric focusing patterns of the synthetic peptide suggest that the peptide is a slightly basic protein.

Example 19: CETP Inhibition by Various Peptide Fragments

A CE transfer assay as described in Example 4 above was conducted using $HDL_1$ baboon plasma, $^3H$ HDL, and the VLDL+LDL carriers, in the presence of CETP enzyme to mediate the exchange.

The reactions were conducted at 37° C. and at 4° C. (control) in duplicate. The results are shown in Table 3 below.

TABLE 3

| CETP Inhibition by Various Peptide Fragments | | | | | |
|---|---|---|---|---|---|
| CETP (µl) | [H³] HDL (µg) | Synthetic Peptide (µg) | VLDL + LDL (µg) | Temp. (°C.) | Inhibition (%) |
| 125 | 100 | | 300 | 37 | 0 |
| 125 | 100 | | 300 | 4 | |
| 125 | 100 | 50 9 amino acid | 300 | 37 | 0 |
| 125 | 100 | | 300 | 4 | |
| 125 | 100 | 50 21 amino acid | 300 | 37 | 4 |
| 125 | 100 | | 300 | 4 | |
| 125 | 100 | 50 36 amino acid | 300 | 37 | 32 |
| 125 | 100 | | 300 | 4 | |
| 125 | 100 | 100 9 amino acid | 300 | 37 | 0 |
| 125 | 100 | | 300 | 4 | |
| 125 | 100 | 100 21 amino acid | 300 | 37 | 26 |
| 125 | 100 | | 300 | 4 | |
| 125 | 100 | 100 36 amino acid | 300 | 37 | 32 |
| 125 | 100 | | 300 | 4 | |

The invention now being fully described, it will be apparent to one of ordinary skill in the art that many changes and modifications may be made thereto without departing from the spirit or scope of the invention as set forth herein.

We claim:

1. A method of preventing atherosclerosis in a mammal being predisposed to that condition, comprising a cholesteryl ester transfer protein inhibitory polypeptide of sequence Asp-Val-Ser-Ser-Ala-Leu-Asp-Lys-Leu-Lys-Glu-Phe-Gly-Asn-Thr-Leu-Glu-Asp-Lys-Ala-Trp-Glu-Val-Ile-Asn-Arg-Ile-Lys-Gln-Ser-Glu-Phe-Pro-Ala-Lys-Thr (SEQ. ID. NO: 1)

wherein the cholesteryl ester transfer protein inhibitory polypeptide has at least one substitute amino acid or amino bond;

the substitute amino acid for Asp being selected from the group consisting of Glu, $C_\alpha$-methylVal;

the substitute amino acid for Val being selected from the group consisting of isoVal, nor Val, Leu, and $C_\alpha$-methylVal;

the substitute amino acid for Ala being selected from the group consisting of Gly, β-Ala, $C_\alpha$-methylAla, and 2-amino butyric acid;

the substitute amino acid for Leu being selected from the group consisting of norLeu, isoLeu, and $C_\alpha$-methylLeu;

the substitute ammo acid for Lys being selected from the group consisting of ornithine, Arg, citrulline and $C_\alpha$-methylLys;

the substitute ammo acid for Gly being selected from the group consisting of Ala and 2-amino isobutyric acid;

the substitute ammo acid for Asn being selected from the group consisting of Gln, citrulline, and $C_\alpha$-methyl Asn;

the substitute ammo acid for Trp being selected from the group consisting of p-benzoylPhe, Arg and $C_\alpha$-methyl Trp;

the substitute amino acid for Glu being selected from the group consisting of 2-amino adipic acid, Asp, and $C_\alpha$-methylGlu;

the substitute amino acid for Ile being selected from the group consisting of Leu, norLeu, and $C_\alpha$-methylLeu;

the substitute amino acid for Arg being selected from the group consisting of Lys, homoArg, citrulline and $C_\alpha$-methylArg;

the substitute amino acid for Gln being selected from the group consisting of Ash, citrulline, and $C_\alpha$-methylGln;

the substitute amino acid for Phe being selected from the group consisting of 2-amino-4-phenylbutyric acid, Leu and $C_\alpha$-methylPhe;

the substitute amino acid for Thr being selected from the group consisting of Ser, Met and $C_\alpha$-methylThr;

the substitute amino acid for Set being selected from the group consisting of Thr and $C_\alpha$-methylSer;

the substitute amino acid for Pro being selected from the group consisting of 3,4-dehydroPro, Ser and $C_\alpha$-methylPro; and the substitute amino acid bond being selected from the group consisting of thioether, alkyl, alkyl amino, and combinations of thioether, alkyl and alkyl amino bonds 2. A method of preventing atherosclerosis in a mammal being predisposed to that condition, comprising administering to the mammal a prophylactically effective amount of a polypeptide consisting of peptide of sequence (SEQ. ID. NO: 1)
Asp—Val—Ser—Ser—Ala—Leu—Asp—Lys—Leu—Lys—Glu—

Phe—Gly—Asn—Thr—Leu—Glu—Asp—Lys—Ala—Trp—Glu—

Val—Ile—Asn—Arg—Ile—Lys—Gln—Ser—Glu—Phe—Pro—

Ala—Lys—Thr.

3. The method of claim 2, wherein the polypeptide is administered in an amount of about 10 to 200 mg every one to two weeks.

4. The method of claim 2, wherein the polypeptide is administered intravenously.

5. The method of claim 2, wherein the mammal is a human.

6. A method of treating a mammal afflicted with atherosclerosis comprising administering to the mammal a therapeutically effective amount of a polypeptide consisting of sequence (SEQ. ID. NO: 1)
Asp—Val—Ser—Ser—Ala—Leu—Asp—Lys—Leu—Lys—Glu—

Phe—Gly—Asn—Thr—Leu—Glu—Asp—Lys—Ala—Trp—Glu—

Val—Ile—Asn—Arg—Ile—Lys—Gln—Ser—Glu—Phe—Pro—

Ala—Lys—Thr.

7. The method of claim 6, wherein the polypeptide is administered in an amount of about 10 to 400 mg every one to two weeks.

8. The method of claim 6, wherein the polypeptide is administered intravenously.

9. The method of claim 6, wherein the mammal is a human.

---

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 36
        ( B ) TYPE: amino acid
        ( C ) STRANDEDNESS:
        ( D ) TOPOLOGY: unknown ( i i ) MOLECULE TYPE: Protein and Peptide ( i i i ) HYPOTHETICAL:

( i v ) ANTI-SENSE:

( v ) FRAGMENT TYPE: N-terminal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:

(G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO: 1:

(xi) SEQUENCE DESCRIPTION: SEQ ID NO: 1:

Asp Val Ser Ser Ala Leu Asp Lys Leu Lys Glu Phe
         1               5                   10

Gly Asn Thr Leu Glu Asp Lys Ala Trp Glu Val Ile
                 15                  20

Asn Arg Ile Lys Gln Ser Glu Phe Pro Ala Lys Thr
         25                  30                  35

10. A method of treating a mammal afflicted with atherosclerosis comprising administering to the mammal a therapeutically effective amount of a cholesteryl ester transfer protein inhibitory polypeptide of sequence Asp-Val-Ser-Ser-Ala-Leu-Asp-Lys-Leu-Lys-Glu-Phe-Gly-Asn-Thr-Leu-Glu-Asp-Lys-Ala-Trp-Glu-Val-Ile-Asn-Arg-Ile-Lys-Gln-Ser-Glu-Phe-Pro-Ala-Lys-Thr (SEQ. ID. NO: 1)

wherein the cholesteryl ester transfer protein inhibitory polypeptide has at least one substitute amino acid or amino bond;

the substitute amino acid for Asp being selected from the group consisting of Glu, $C_\alpha$-methylVal;

the substitute amino acid for Val being selected from the group consisting of isoVal, nor Val, Leu, and $C_\alpha$-methylVal;

the substitute amino acid for Ala being selected from the group consisting of Gly, β-Ala, $C_\alpha$-methylAla, and 2-amino butyric acid;

the substitute amino acide for Leu being selected from the group consisting of norLeu, isoLeu, and $C_\alpha$-methylLeu;

the substitute amino acid for Lys being selected from the group consisting of ornithine, Arg, citrulline and $C_\alpha$-methylLys;

the substitute amino acid for Gly being selected from the group consisting of Ala and 2-amino isobutyric acid;

the substitute amino acid for Asn being selected from the group consisting of Gln, citrulline, and $C_\alpha$-methyl Asn;

the substitute amino acid for Trp being selected from the group consisting of p-benzoyl Phe, Arg and $C_\alpha$-methyl Trp;

the substitute amino acid for Glu being selected from the group consisting of 2-amino adipic acid, Asp, and $C_\alpha$-methylGlu;

the substitute amino acid for He being selected from the group consisting of Leu, norLeu, and $C_\alpha$-methylLeu;

the substitute amino acid for Arg being selected from the group consisting of Lys, homoArg, citrulline and $C_\alpha$-methylArg;

the substitute amino acid for Gln being selected from the group consisting of Ash, citrulline, and $C_\alpha$-methylGln;

the substitute amino acid for Phe being selected from the group consisting of 2-amino-4-phenyl butyric acid, Leu and $C_\alpha$-methylPhe;

the substitute amino acid for Thr being selected from the group consisting of Ser, Met and $C_\alpha$-methylThr;

the substitute amino acid for Ser being selected from the group consisting of Thr and $C_\alpha$-methylSer;

the substitute amino acid for Pro being selected from the group consisting of 3,4-dehydroPro, Set and $C_\alpha$-methylPro; and the substitute amino acid bond being selected from the group consisting of thioether, alkyl, alkyl amino, and combinations of thioether, alkyl and alkyl amino bonds. g1 administering to the mammal a prophylactically effective amount of

* * * * *

UNITED STATES PATENT AND TRADEMARK OFFICE
CERTIFICATE OF CORRECTION

| | | |
|---|---|---|
| PATENT NO. | : 5,512,548 | Page 1 of 1 |
| APPLICATION NO. | : 08/193515 | |
| DATED | : April 30, 1996 | |
| INVENTOR(S) | : Rampratap Kushwaha et al. | |

It is certified that error appears in the above-identified patent and that said Letters Patent is hereby corrected as shown below:

Column 1, Lines 13-17 omit

"The work leading to the present invention was partially supported by National Heart, Lung and Blood Institute Grants Nos. HL28972 and HL41256, and Contract No. HV53030. The government may hold rights in the present patent."

replace with

"This invention was made with government support under Grant Numbers HL28972 and HL41256, and Contract No. HV53030 awarded by the National Institutes of Health. The government has certain rights in the invention."

Signed and Sealed this
Twenty-fifth Day of September, 2012

David J. Kappos
*Director of the United States Patent and Trademark Office*